United States Patent [19]
Steele et al.

[11] Patent Number: 6,090,348
[45] Date of Patent: *Jul. 18, 2000

[54] METHOD FOR PROGRAMMING AN ELECTRONIC PIPETTER

[75] Inventors: Timothy P. Steele, Augusta; Michael G. Daniels, Denville, both of N.J.

[73] Assignee: Becton, Dickinson and Company, Franklin Lakes, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/818,214

[22] Filed: Mar. 14, 1997

[51] Int. Cl.⁷ ....................................................... B01L 3/02
[52] U.S. Cl. ............................ 422/67; 422/100; 73/1.74; 73/864.11
[58] Field of Search ................................ 422/62, 63, 67, 422/100; 436/180, 179; 73/1.74, 863.01, 864.01, 864.11

[56] References Cited

U.S. PATENT DOCUMENTS

| 4,821,586 | 4/1989 | Scordato et al. . |
| 5,294,405 | 3/1994 | Kenney .................................... 422/103 |

OTHER PUBLICATIONS

Cole–Parmer Instrument Company, Biohit Proline Electronic Pipettors, p. 278, 1993.

*Primary Examiner*—Elizabeth McKane
*Attorney, Agent, or Firm*—Arthur D. Dawson

[57] ABSTRACT

A method for programming an electronic pipetter to provide more precise measurement and dispensing is provided, as well as an improved display for displaying clearly and in detail the programming steps and options to the user thereof. The electronic pipetter may be operated in one of five modes, including a manual mode, a quick-shot mode, a multi-dispense mode, a sequential-dispense mode and a hands-free mode.

1 Claim, 10 Drawing Sheets

▲ ▼     ARROWS INDICATING THE DIRECTION OF FLUID FLOW, ENTER IN DATA FOR "▲" FOR ASPIRATING OR "▼" FOR DISPENSING ENTRIES.

AL     DISPENSING ALIQUOT SIZE NEEDS TO BE SELECTED FOR MODE.

?     INDICATES TO YOU THAT THE PIPETTER REQUIRES INFORMATION FROM YOU.

INDICATES THAT YOU MAY ENTER OR CHANGE THIS BLINKING ITEM. USE SCROLL BARS TO CHANGE, THEN PRESS [E]. (  SYMBOLIZES BLINKING.)

SP     INDICATES SPEED CHANGE. (PLEASE TAKE NOTE OF YOUR DIRECTIONAL FLUID ARROWS.)

bLoOut     REQUIRES YOU TO EXPEL EXCESS FLUID BEFORE REFILLING. CLICK THE BOTTOM OPERATING BUTTON A SECOND TIME TO EXPEL THE RESIDUE.

bEG In     TELLS YOU ALL DATA HAS BEEN ENTERED AND YOU MAY PRESS OPERATING BUTTON TO ACTIVATE THE PROGRAM.

CY ?     THE NUMBER OF CYCLES YOU'LL REQUIRE FOR HANDS-FREE MODE (1-99).

▲dELA     DELAY TIME BETWEEN ASPIRATION CYCLES IN THE HANDS-FREE MODE.

▼dELY     DELAY TIME BETWEEN EACH DISPENSED ALIQUOT IN THE HANDS-FREE MODE.

▼bdLY     TIME DELAY BEFORE BLOWOUT OCCURS IN HANDS-FREE MODE.

Err     THE SOFTWARE HAS AN ERROR OR PROBLEM.

PG     CONFIRMS YOU ARE IN THE MEMORY MODE OPTION, AND PROGRAM SELECTION IS NECESSARY (001,002,003).

METHOD FOR PROGRAMMING AN ELECTRONIC PIPETTER

BACKGROUND OF THE INVENTION

1. Field of the Invention

The invention is in the field of electronic pipetters. In particular, the invention relates to a method for programming an electronic pipetter.

2. Description of Related Art

A conventional mechanical pipet is usually a small piece of apparatus with which fluids are transferred, measured, absorbed, etc., as in chemical operations. The simplest form is a narrow glass tube, such as an eyedropper, the liquid being drawn up into it by suction (aspiration) and retained by closing the upper end. The liquid can then be dispensed in measured, equal fractional amounts, called aliquots. For example, if the pipet contains 25 ml of liquid, 8 aliquots of 3 ml of liquid can be dispensed, with 1 ml of liquid left over.

More recently, a computer-controlled electronic pipetter has been developed to aspirate and dispense various liquid media through an attached pipette. This computer-controlled electronic pipetter has a user interface consisting of a liquid crystal display (LCD) and programming keys. However, the methodology for programming this pipetter is difficult to use, because the order of programming commands is neither intuitive nor easy to remember, and the displayed aspirating and dispensing parameters required to be set or selected in any given programming step are often difficult to understand or ambiguous. This forces the users to rely extensively on product manuals to learn and relearn the correct programming methodology, especially when the user has not used the existing electronic pipetter in weeks or months. Moreover, because there is no intuitive programming methodology with respect to the complexity of the desired operational mode in the existing electronic pipetter, new users are often intimidated by the immediate complex programming requirements when first turning on the existing electronic pipetter, discouraging their further use of such a pipetter. In addition, the existing electronic pipetter does not provide the user with a simple, single-parameter "quick-shot" programming mode or a multiple aspiration-dispensation "hands-free" operating mode.

The information displayed on the LCD of the existing electronic pipetter is generally limited to single letters or initials to indicate, in a non-intuitive fashion, the operational modes and status of the pipetter. Moreover, this LCD can only display a limited number of characters, each corresponding to several control functions, thus creating ambiguities. The functions can only be displayed one at a time, making selection of any one function difficult. For example, the same characters are used to display the selected operating mode and to display the selected number of aliquots to be dispensed. When one of those two parameters is displayed, the other is not. If the user wishes to examine or reset the other non-displayed parameter, the user must switch between the displays, which is not only inconvenient, but is often difficult since the user's fingers are usually otherwise occupied conducting the pipetting operation. Further, the LCD of the existing pipetter simply does not offer any guidance on which programming step comes next when a sequence of steps must be entered.

In summary, because of the above-described programming and display limitations in the existing electronic pipetter, measurement and dispensing precision suffers, causing variability between the aliquots of dispensed liquid. Therefore, despite the current availability of an electronic pipetter with an LCD and keys for programming, there is still a need for a more user-friendly, easy-to-program electronic pipetter. In particular, there is a need for an electronic pipetter having an advanced programming methodology and an easy-to-understand display so that the user can more exactly and quickly control the electronic pipetter, which in turn provides more precise, repeatable measuring and dispensing of fluids. An improved electronic pipetter is especially needed by those users who prepare large numbers of tissue cultures, in which aliquot precision and repeatability is absolutely demanded.

SUMMARY OF THE INVENTION

It is an object of the present invention to provide a method for programming an electronic pipetter to provide precise measurement and dispensing.

It is another object of the present invention to provide an improved display for displaying clearly and in detail the programming steps and options to the user of an electronic pipetter.

In one aspect of the present invention, a manual mode of operating an electronic pipetter is provided, wherein a first operating button aspirates a fluid through an attached pipet and a second operating button dispenses the fluid through the attached pipet. No programming is required for the manual operating mode.

In another aspect of the present invention, four programming modes are provided, wherein the operator programs the pipetter through a plurality of programming keys electrically connected to the computer, and is guided by information presented on an LCD display. These four programming modes include a quick-shot mode, a multi-dispense mode, a sequential-dispense mode and a hands-free mode. The operator programs the desired mode and the modes' operating parameters, which may include pipet size, dispensing aliquot volume, number of aspiration/dispensing cycles, and various time delays.

In yet another aspect of the present invention, a memory is also provided to store the programmed operating parameters of the multi-dispense mode, a sequential-dispense mode and a hands-free mode. The stored parameters may be retrieved by the operator to enable operation without reprogramming.

BRIEF DESCRIPTION OF THE DRAWINGS

These and other features and advantages of the present invention can best be understood by reference to the detailed description of the preferred embodiments set forth below taken with the drawings, in which.

DETAILED DESCRIPTION OF THE PREFERRED EMBODIMENTS

Figure 1:
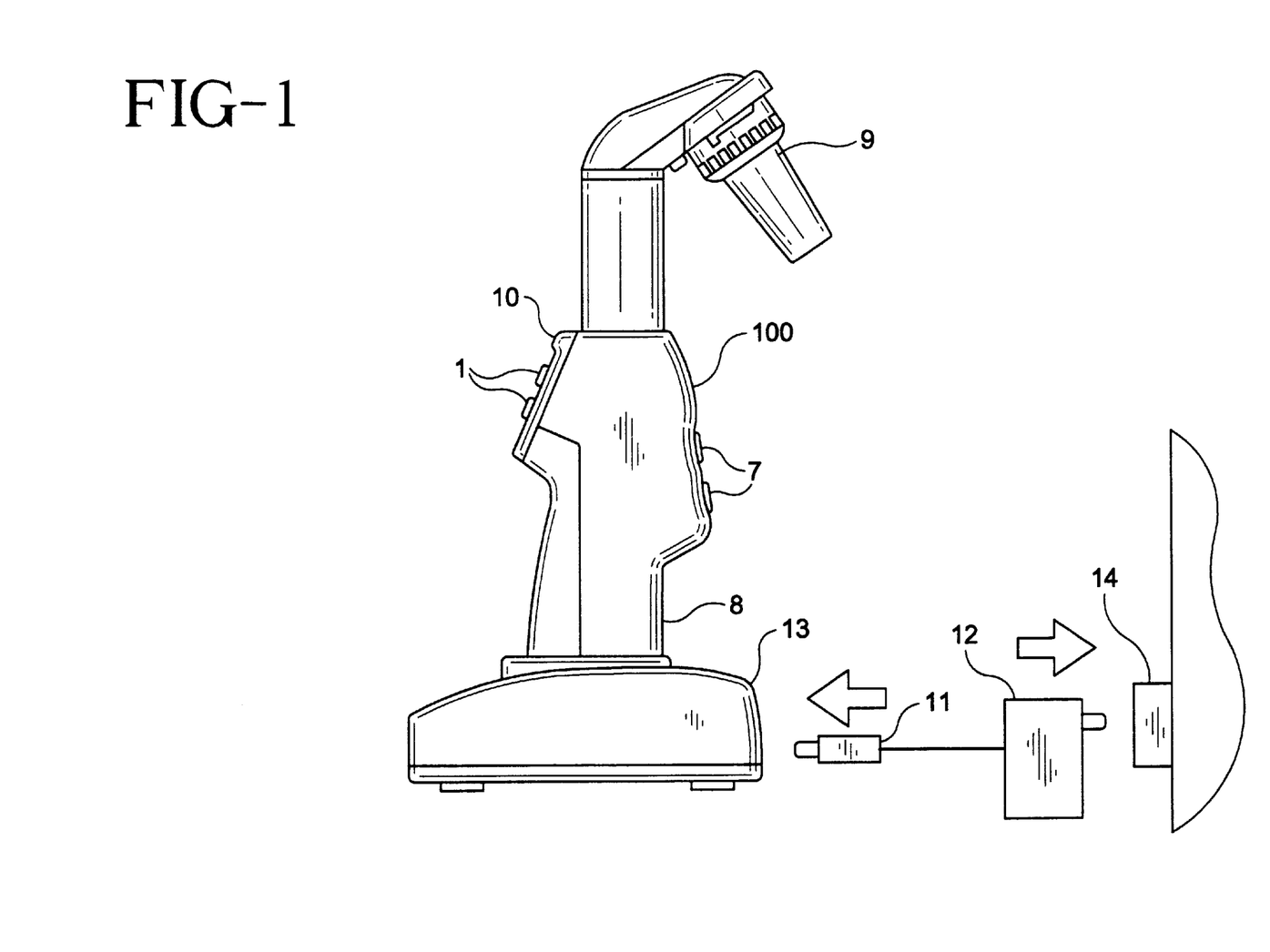
FIG. 1 is a side view of an electronic pipetter and its charging components.

The outside of the pipetter 100 includes a keypad with a plurality of programming keys 1, a plurality of operating buttons 7 (preferably two), a handle for holding the pipetter 8, a nosepiece assembly 9 and an LCD display 10, as shown in FIG. 1. The programming keys 1, operating buttons 7 and LCD display 10 are all electrically connected to a microprocessor computer internal to the pipetter.

The microprocessor can be programmed, as discussed in more detail below, by the operator via pressing a sequence of programming keys, to control the aspirating and dispensing operations of the pipetter. The microprocessor generates signals to start and stop the aspirating and dispensing mechanism internal to the pipetter. Aspirating and dispensing mechanisms are substantially known in the art (see, for example, U.S. Pat. Nos. 5,505,097 and 5,343,769) and therefore will not be described further herein. The microprocessor generates the controls signals based on the operator-selected operating mode, the operator-selected aspirating and dispensing parameters and the pressing of the operating buttons.

Two operating buttons 7 are located on the front handle 8 of the pipetter. Preferably, the top operating button is used to activate aspiration, while the bottom operating button allows for dispensing. In some of the automated modes of operation, however, either the top or bottom button may be used to activate the aspiration and dispensing operations. The operating buttons generally only require a quick downward press and then immediate release by the operator to activate the pipetter.

The programming keys 1 include, but are not limited to, (1) a mode key for selecting one of the available operating modes; (2) an enter key for entering all the programming information into the computer; (3) a down scroll key and (4) an up scroll key for scrolling through ranges of pipet sizes, dispensing aliquot volumes and aspirating and dispensing speeds, and for selecting a desired pipet size, aliquot volume or aspirating or dispensing speed; (5) a speed key to change aspirating and/or dispensing speed settings; and (6) an "oops" key for clearing one or more previous programming steps, as shown in FIG. 2.

Figure 2:
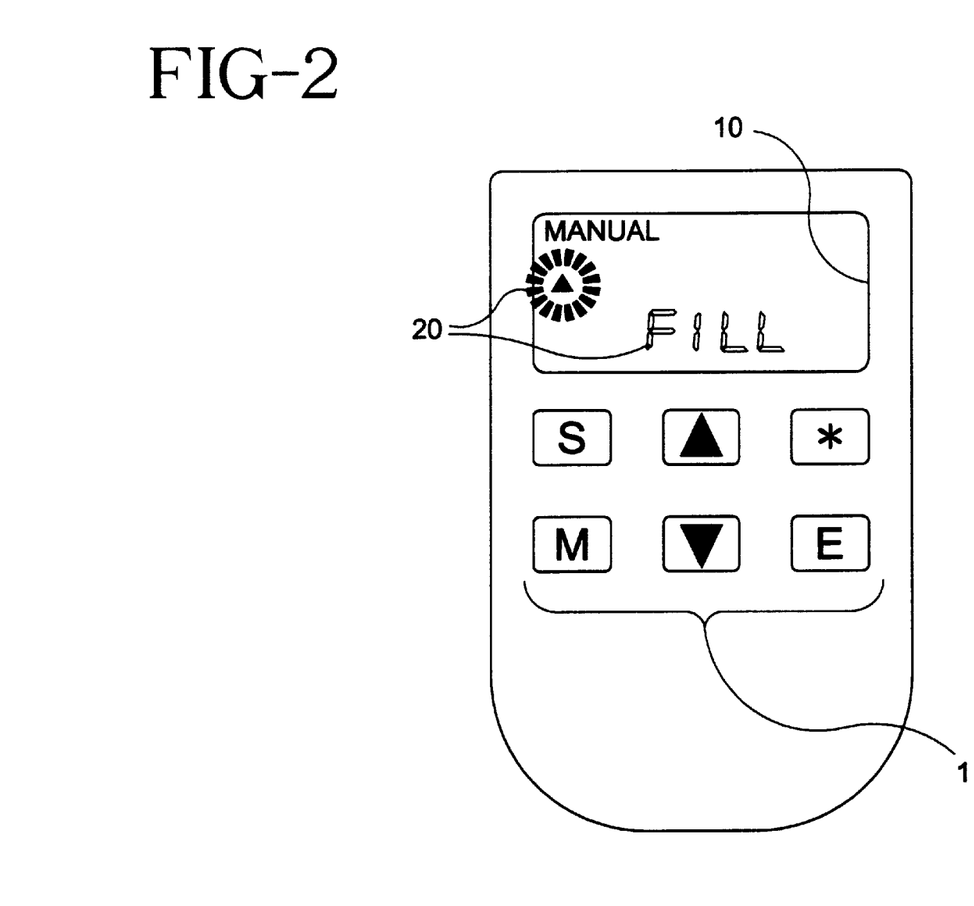
FIG. 2 depicts programming keys and LCD display of the present invention.
Figure 3:
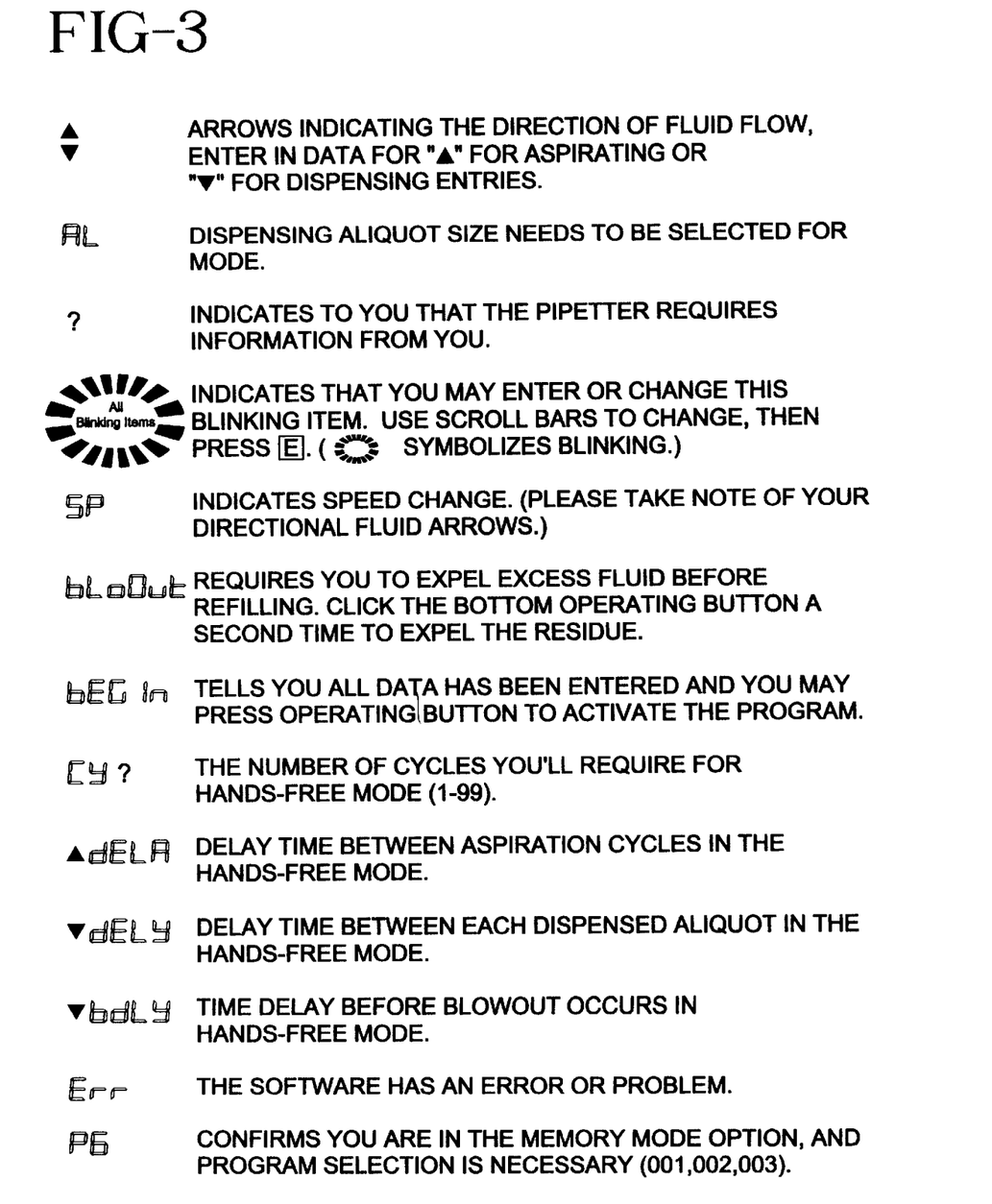
FIG. 3 is a table of the LCD symbols used in the present invention.

An improved LCD 10, also shown in FIG. 2, provides numerous easy-to-understand, intuitive symbols 20, to both guide the operator when programming the pipetter and display the status of the pipetter. Some examples of the LCD symbols are shown in the table of FIG. 3.

Figure 4:
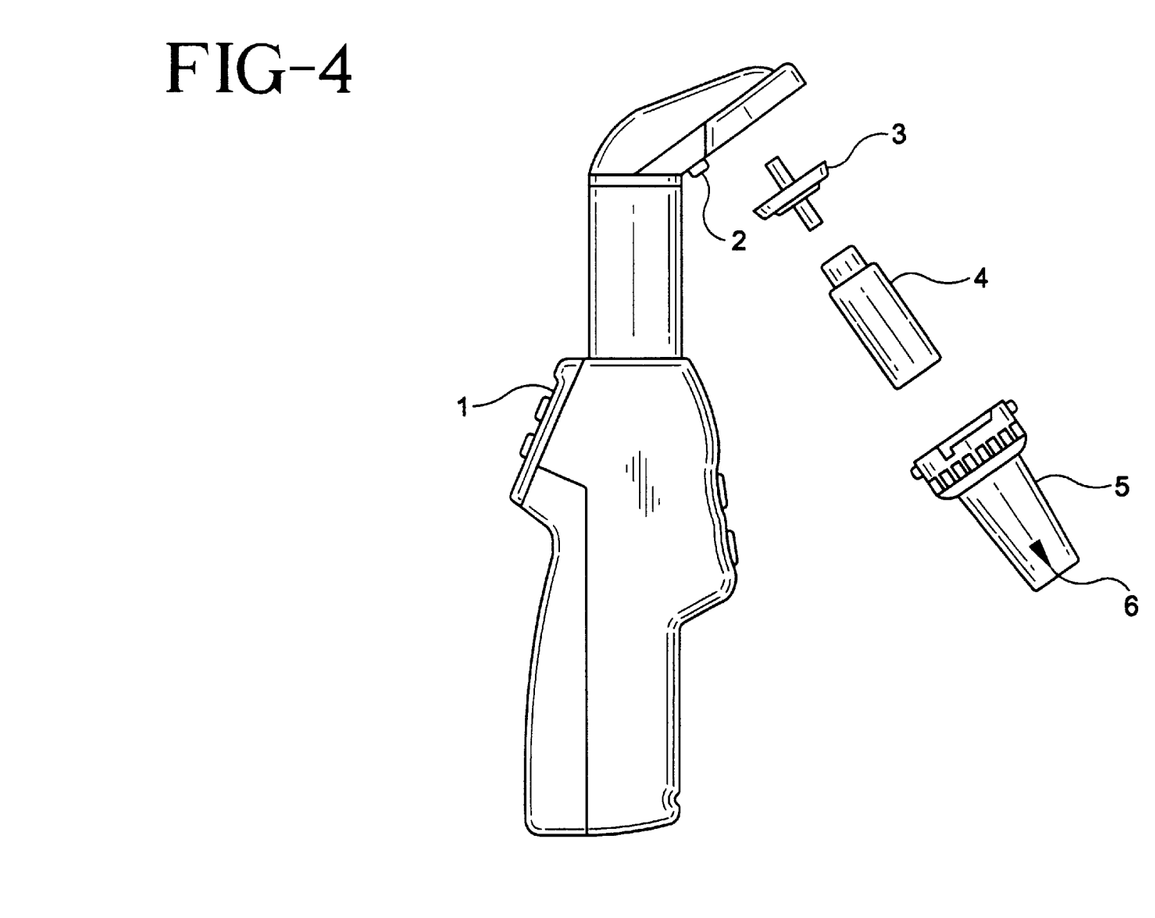
FIG. 4 is an exploded view of an electronic pipetter and its nosepiece assembly.

The electronic pipetter preferably is used with various size nosepieces (5 ml and 10 ml), rubber inserts and various size disposable tips (5 ml and 10 ml) or plastic or glass pipets (1, 2, 5, 10 or 25 ml). The nosepiece assembly 9 includes filter 3, rubber insert 4, and nosepiece 5 with graduation alignment marker 6, attached to the pipetter as shown in FIG. 4. To attach the nosepiece components, the operator press the nosepiece lock releasing means 2, such as a button, inserts the nosepiece 5 and rotates the nosepiece to the right. Rubber inserts and filters may be changed in the same manner. The rubber insert 4 enables the attached pipet or tip to fit securely in place, thus creating the proper vacuum level required for aspiration and reducing leakage. Filter 3 protect the pipetter from accidental over-aspiration.

The pipetter, including the microprocessor, program memory, and aspirating and dispensing mechanisms, is preferably powered by a rechargeable battery (NiCad, 600 mAh capacity, 4.8 V), although other conventional power sources may be used. To recharge the rechargeable battery in the pipetter, an output plug 11 of a transformer 12 is inserted into a charging base 13, as shown in FIG. 1. The outlet prongs of the transformer are then inserted into an AC power supply (wall outlet 14), the input voltage of transformer being the same as the AC power supply voltage. A green light on the charging base indicates that power is being supplied to the charging base. The pipetter is then inserted into the charging base to charge the rechargeable battery. Preferably, the pipetter is turned on at all times, even when being recharged, since switching off the pipetter will cause any programs stored in the pipetters memory (see below) to be lost. In general, the pipetter should only be turned off if it is being stored for more than one week. When fully charged, as indicated by the LCD display on the pipetter, the pipetter is capable of aspirating and dispensing a large number, for example, 500 cycles. When the battery is almost discharged, the LCD will display a low battery message to the operator, indicating the need to recharge the unit. The pipetter should then be returned to the charging base, even though the pipetter is capable of additional use for a short period of time.

The operation of the operating modes is briefly described in the flow charts of FIGS. 5a–5f, and in more detail below.

Figure 5A:
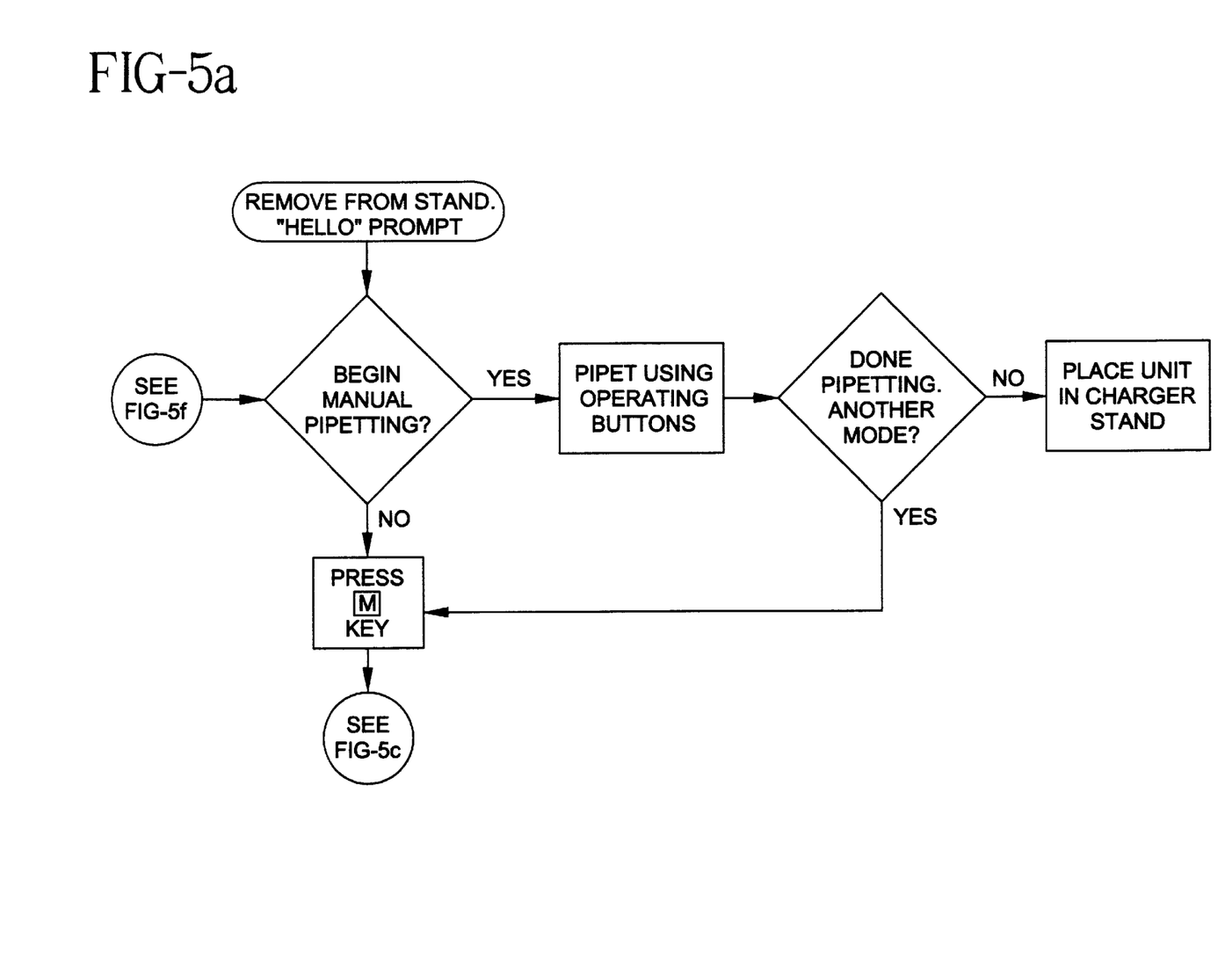
FIG. 5a is a flow chart describing the operation of a first embodiment of the present invention.

In a first embodiment of the present invention, an electronic pipetter is provided that is capable of operating in a manual mode (FIG. 5a). In this mode, the aspirating and dispensing modes are controlled manually, similar to a mechanical pipetter, and no programming by the operator is needed. The operator removes the turned on pipetter from the charging base, which causes the computer to display a greeting, indicating that the pipetter is operational. Preferably, the pipetter defaults into this manual mode, thus making the simplest use of the pipetter the first operational mode. Thus, unlike existing pipetters, new users will not be intimidated by any immediate complex programming requirements when first turning on the electronic pipetter, and will thus not be discouraged from using the pipetter further.

Figure 5B:
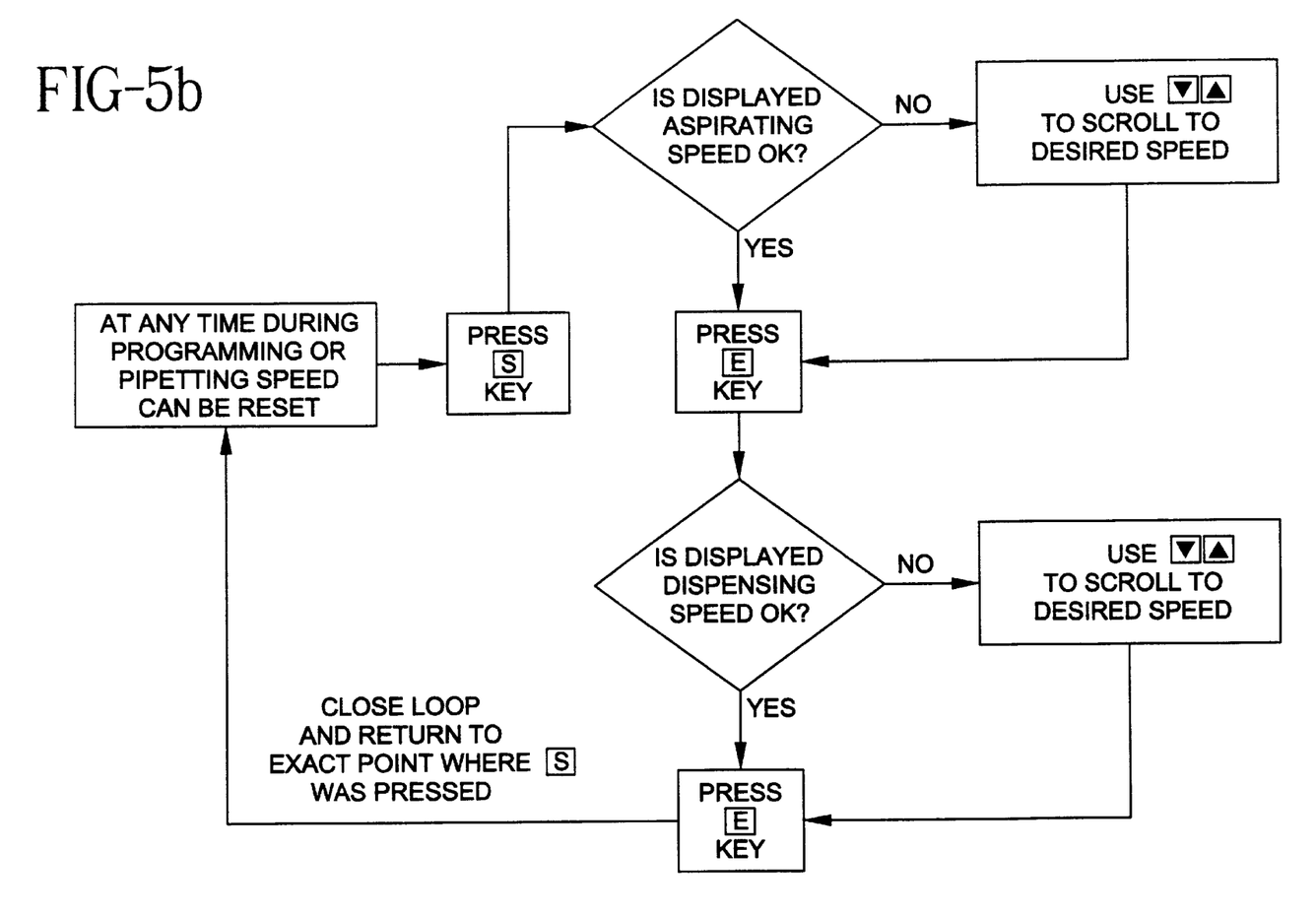
FIG. 5b is a flow chart describing the change of speed operations that may be used in all embodiments of the present invention.

After the pipetter enters the manual mode, a "fill" symbol is displayed to encourage the operator to begin aspirating. At this time, the operator may wish to change the default speed of aspiration and dispensing. As shown in FIG. 5b, the operator may do this by pressing the "S" programming key, causing a blinking "up" arrow to be displayed together with a "SP?" (speed?) query. To change the aspirating speed. the operator simply presses the up scroll key to increase the speed, or the down scroll button to decrease the speed. After the desired aspirating speed has been selected, the operator presses the enter key. When a blinking "down" arrow is displayed, the dispensing speed may be changed in similar fashion to the aspirating speed. This change of speed capability is also available in the other operating modes of the present invention.

The operator then submerges the attached tip or pipet into the liquid medium for aspiration. The operator then simply presses the aspiration operating (top) button to cause aspiration. The computer then commands the aspirating mechanism to begin creating a vacuum, which sucks the liquid into the pipet. After the liquid has been sucked into the pipet, the operator removes the pipet from the liquid. The operator then aims the pipet at, for example, the tissue culture petri dish, and dispenses the aspirated liquid medium into the dish by pressing the dispensing operating (bottom) button. Pushing this button causes the computer to generate a command to the dispensing mechanism to begin dispensing the liquid out of pipet. Any excess fluid remaining in the pipet can be expelled or "blown-out" by pressing the dispensing button a second time, which causes the computer to generate a command to the dispensing mechanism to mechanism out all remaining fluid.

Aspirating and dispensing speed may be alternatively controlled by making the operating buttons sensitive to applied finger pressure. The change in finger pressure causes the computer to control the aspiration and dispensing speeds as follows: the harder the aspirating button is pressed, the higher the aspirating speed, and the harder the dispensing button is pressed, the higher the dispensing speed.

Figure 5C:
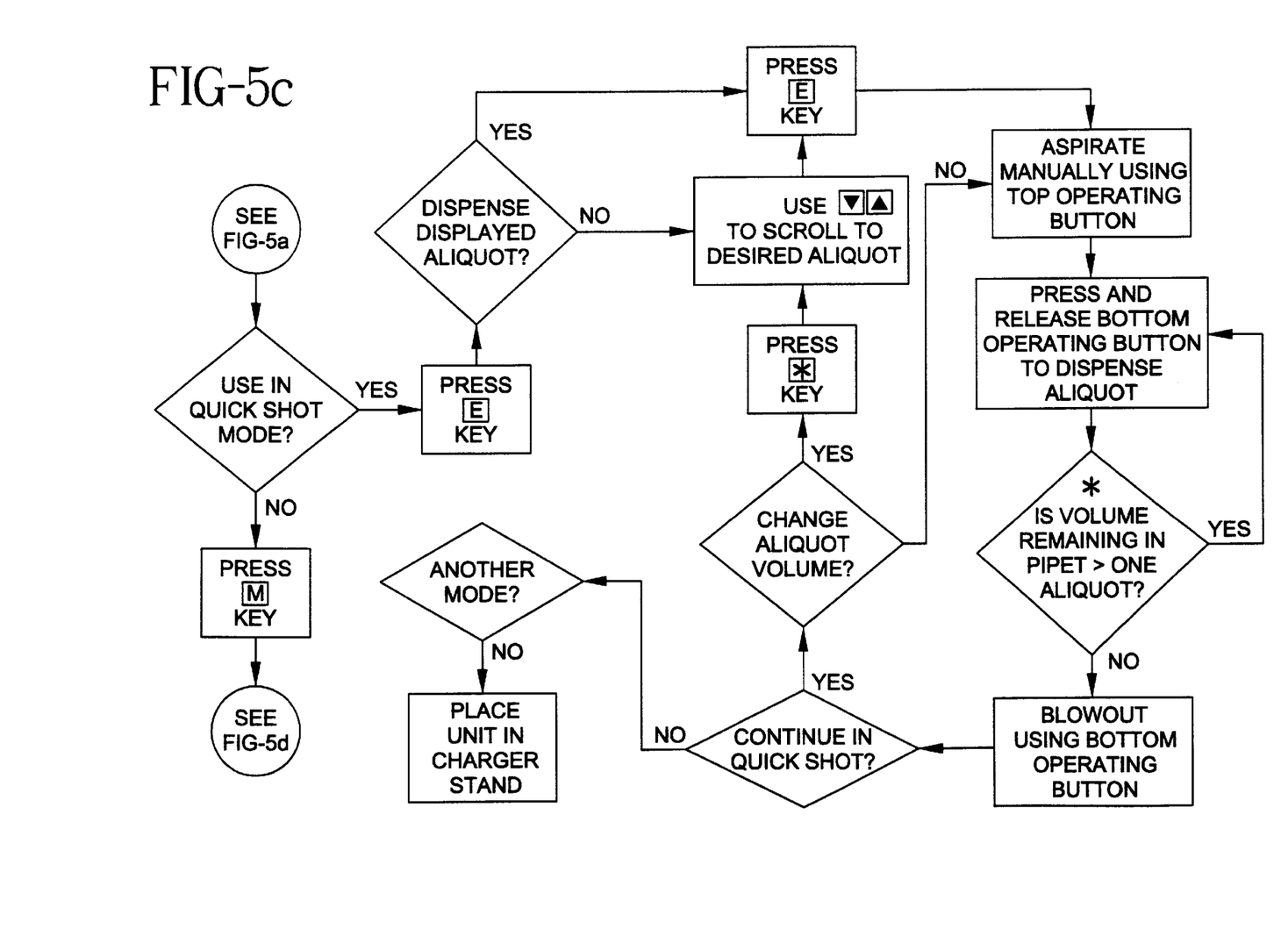
FIG. 5c is a flow chart describing the operation of a second embodiment of the present invention.

In a second embodiment of the present invention, as shown in FIG. 5c, an electronic pipetter is provided that is capable of operating in a manual aspirating, programmed dispensing ("quick-shot") mode, in which the operator programs the pipetter to a desired aliquot volume. This mode requires programming by the operator and is thus a little more complicated than the manual mode. It is thus preferably and intuitively provided as the second operating mode, after the default manual mode, to the operator.

To enter the quick shot mode, the operator presses the mode key until the quick shot mode symbol appears on the LCD. The operator then presses the enter key to enter the quick shot mode into the computer. Next, the LCD asks the operator to program the dispensing aliquot volume. To locate the desired dispensing aliquot volume, the operator presses the down or up scroll keys. After the operator has selected the dispensing aliquot volume, the operator presses the enter key to enter that information into the computer. This causes computer to display on the LCD the "fill" symbol, which tells the operator that the aspiration may begin. The operator then submerges the pipette into the liquid medium and aspirates the liquid medium by pressing the aspirating operating button as in the manual mode described above. Because aspiration is manually controlled, it is preferable that the operator attaches a large pipet, such as a 25 ml pipet, to the pipetter to match the largest volume that can be aspirated to prevent overfilling and wetting out of the filter.

After the pipet is manually filled, the operator preferably keeps the pipet in the media bottle and presses the dispensing button once. This will dispense a small amount of fluid. The operator then removes the pipet from the media bottle. The LCD will now be caused to display the available number of aliquots. The operator then presses and releases the dispensing button to cause the computer to generate a control signal to the dispensing mechanism to dispense a single aliquot of the aspirated liquid. After each aliquot is dispensed, the LCD displays the remaining number of aliquots by deducting one aliquot from the last displayed number. After the last full aliquot is dispensed, the LCD displays a "blowout" symbol, and any excess fluid remaining in the pipet can be blown-out by pressing the dispensing button one additional time as described above.

Figure 5D:
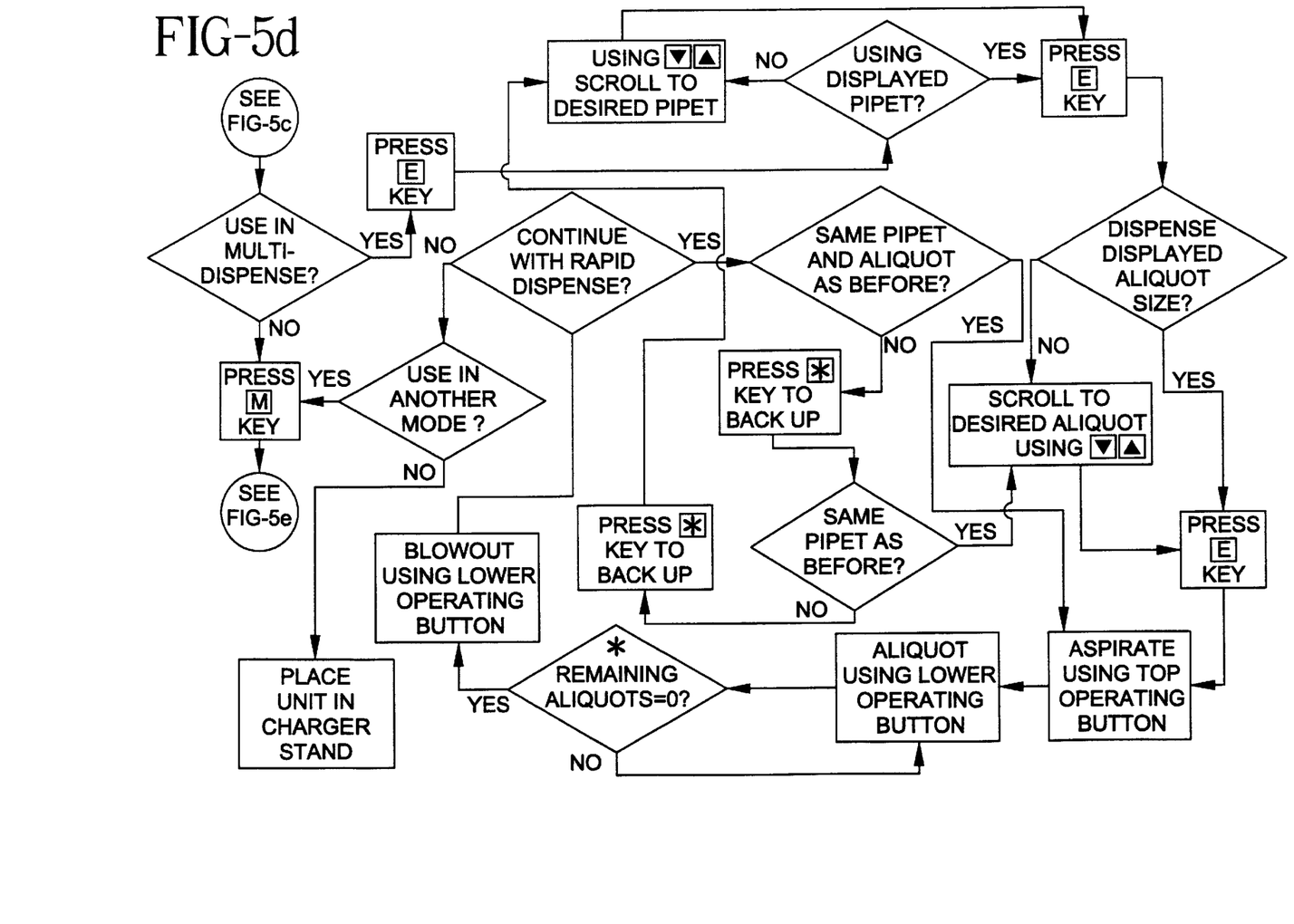
FIG. 5d is a flow chart describing the operation of a third embodiment of the present invention.

In a third embodiment of the present invention, as shown in FIG. 5d, an electronic pipetter is provided that is capable of operating in a programmed aspirating and dispensing ("multi-dispense") mode. The operator programs both a desired pipet size and a required dispensing aliquot volume. This mode requires more programming by the operator than the quick-shot mode and is thus a little more complicated than that mode. It is thus preferably presented as the third operating mode after the quick-shot mode, to the operator.

To enter the multi-dispense mode, the operator presses the mode key until the multi-dispense mode symbol appears on the LCD. The operator then presses the enter key to enter the multi-dispense mode into the computer. Next, the LCD asks the operator to program the desired pipet size. To locate the desired pipet size, the operator presses the down or up scroll keys. After the operator has selected the pipet size, the operator presses the enter key to enter that information into the computer. Next, the LCD asks the operator to program the dispensing aliquot volume. To locate the desired dispensing aliquot volume, the operator presses the down or up scroll keys. After the operator has selected the dispensing aliquot volume, the operator presses the enter key to enter that information into the computer. In addition, if at any time during programming the operator makes a mistake, or wants to change the selection, the operator simply presses the "oops" key, and then reselects and reenters the pipet size or dispensing aliquot volume.

After the aliquot information has been entered into the computer, the computer causes the LCD to display the "fill" symbol, which tells the operator that the aspiration may begin. The operator then submerges the pipette into the liquid medium and aspirates the liquid medium by pressing either the aspirating button or the dispensing button. The computer now generates control signals to cause the aspirating mechanism to fill the pipet with the precise fluid volume automatically.

After the pipet is automatically filled, the computer will automatically compute and display the number of available aliquots. The operator then removes the pipet from the media bottle and presses and releases either the aspirating button or the dispensing button to cause the computer to generate a control signal to the dispensing mechanism to dispense a single aliquot of the aspirated liquid. After each aliquot is dispensed by repressing and rereleasing either operating button, the LCD displays the remaining number of aliquots by deducting one aliquot from the last displayed number. After the last full aliquot is dispensed, the LCD displays a "blowout" symbol, and any excess fluid remaining in the pipet can be blown-out by pressing the dispensing button one additional time as described above.

Figure 5E:
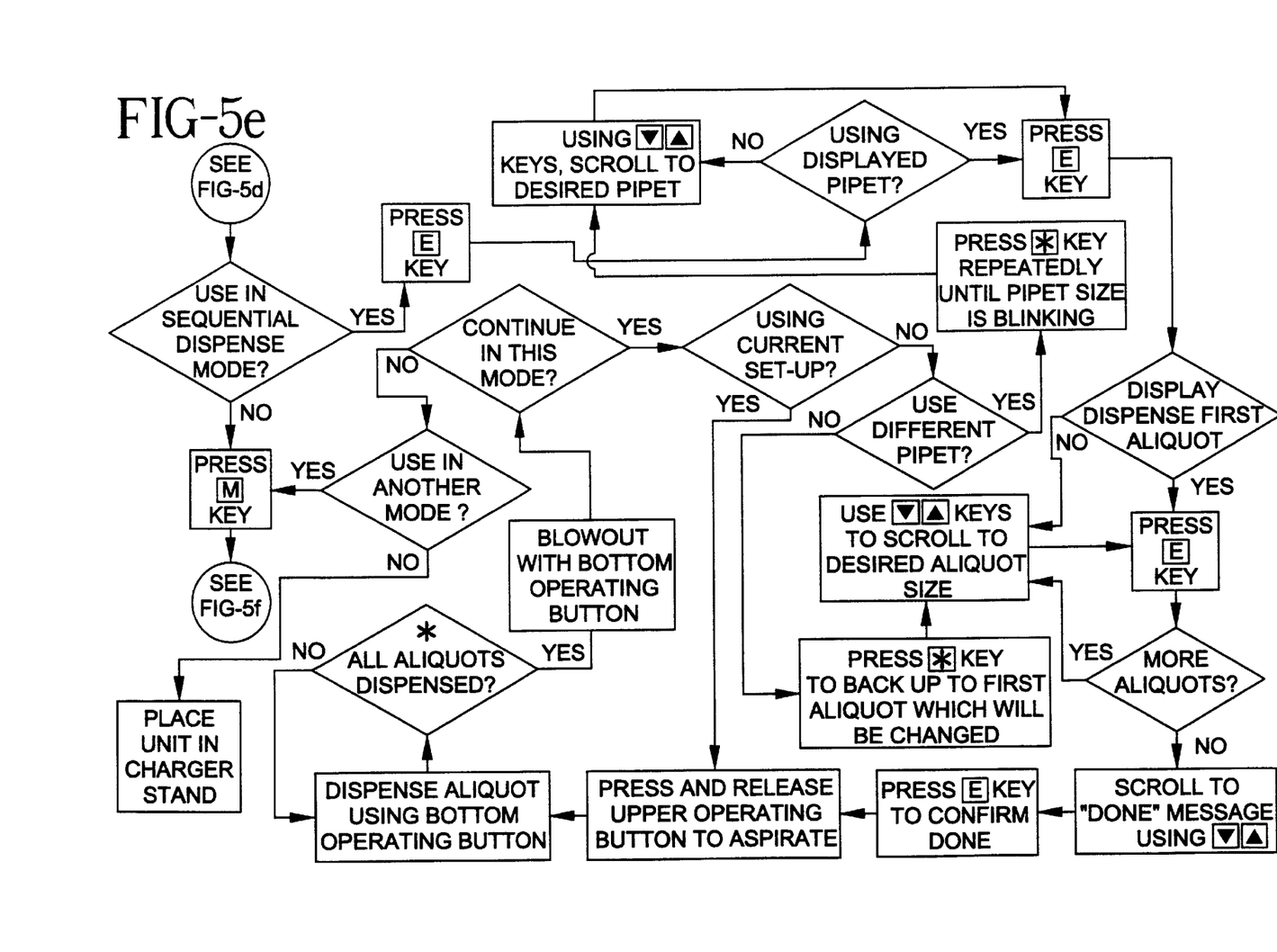
FIG. 5e is a flow chart describing the operation of a fourth embodiment of the present invention.

In a fourth embodiment of the present invention, as shown in FIG. 5e, an electronic pipetter is provided that is capable of operating in a programmed aspirating and dispensing ("sequential-dispense") mode. In this mode, the operator programs the pipetter to individually dispense aliquots of various volumes, in any desired sequence. This mode requires more programming by the operator than the multi-dispense mode and is thus a little more complicated than that mode. It is thus preferably presented to the operator as the fourth operating mode after the multi-dispense mode.

To enter the sequential-dispense mode, the operator presses the mode key until the sequential-dispense mode symbol appears on the LCD The operator then presses the enter key to enter the sequential-dispense mode into the computer. Next, the LCD asks the operator to program the desired pipet size. To locate the desired pipet size, the operator presses the down or up scroll keys. After the operator has selected the pipet size, the operator presses the enter key to enter that information into the computer.

Next, the LCD asks the operator to program the first dispensing aliquot volume. To locate the first desired dispensing aliquot volume, the operator presses the down or up scroll keys. After the operator has selected the first dispensing aliquot volume, the operator presses the enter key to enter that information into the computer. Next, the LCD asks the operator to program the second dispensing aliquot volume. As before, to locate the second desired dispensing aliquot volume, the operator presses the down or up scroll keys. After the operator has selected the second dispensing aliquot volume, the operator presses the enter key to enter that information into the computer. The computer then causes the LCD to display a "done" symbol. The operator is now free to enter as many additional aliquot volumes, up to the pipet volume, by using the up scroll key and enter key in succession. Upon completing all the aliquot entries, the operator presses the enter key again to complete the programming, sequence. As before, if at any time during programming the operator makes a mistake, or wants to change the selected aliquot at any time, the operator simply presses the "oops" key, and then reselects and reenters the dispensing aliquot volume.

After all the aliquot information has been entered into the computer, the computer causes the LCD to display the "fill" symbol, which tells the operator that the aspiration may begin. The operator then submerges the pipette into the liquid medium and aspirates the liquid medium by pressing either operating button. The computer now generates control signals to cause the aspirating mechanism to fill the pipet with the precise fluid volume automatically.

After the pipet is automatically filled, the computer will automatically display the first programmed aliquot. The operator then removes the pipet from the media bottle and presses and releases either the operating button to cause the computer to generate a control signal to the dispensing mechanism to dispense the first aliquot. After the first aliquot is dispensed the LCD displays the second programmed aliquot, which in turn is dispensed by repressing and rereleasing either operating button. The third aliquot, if any, is then displayed and dispensed in the same manner, and so on. After the last programmed aliquot is dispensed, the LCD displays a "blowout" symbol, and any excess fluid remaining in the pipet can be blown-out by double clicking the dispensing button.

Figure 5F:
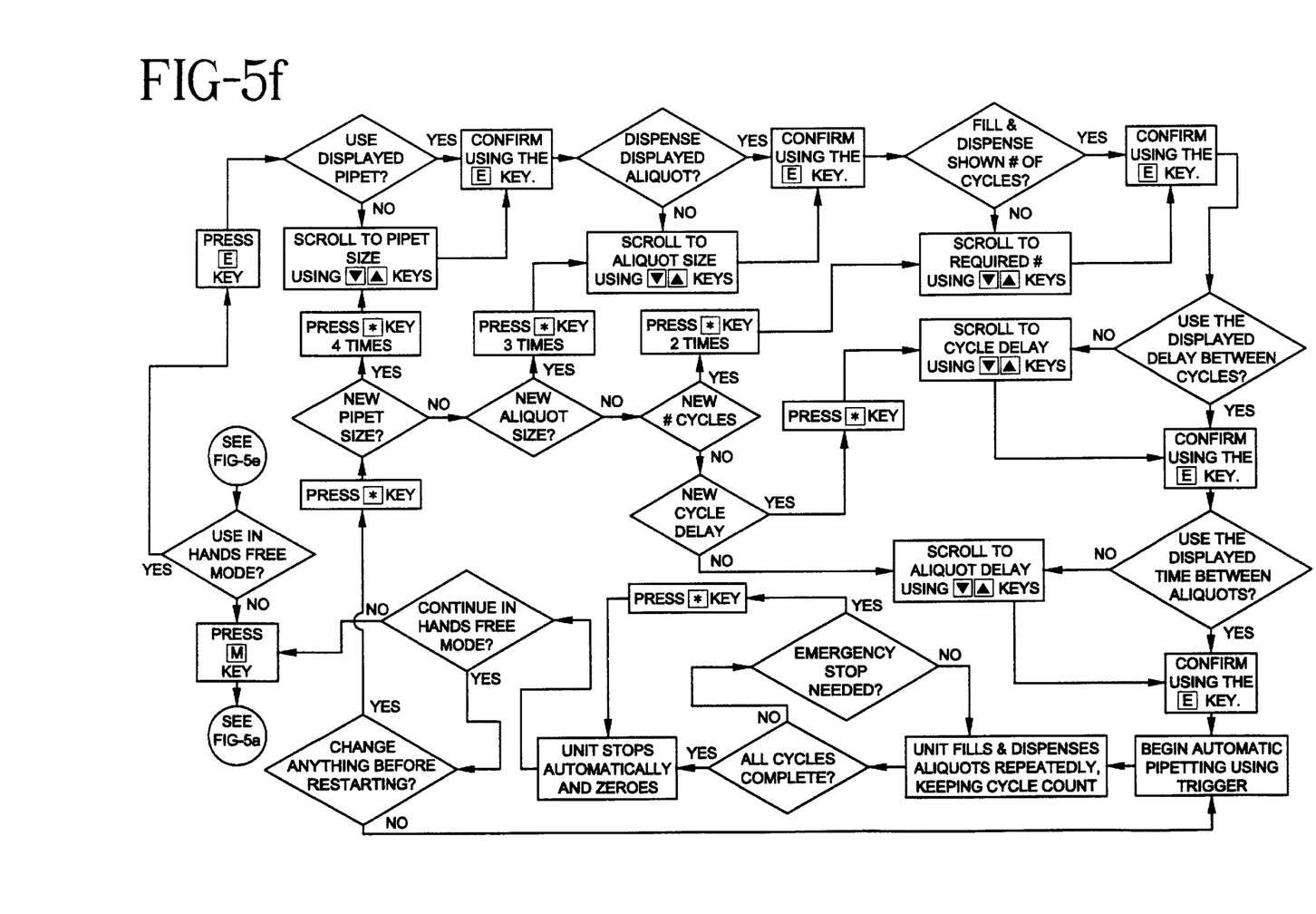
FIG. 5f is a flow chart describing the operation of a fifth embodiment of the present invention.

In a fifth embodiment of the present invention, as shown in FIG. 5f, an electronic pipetter is provided that is capable of operating in a programmed aspirating and dispensing ("hands-free") mode. The operator programs the pipetter to control media aspirations, dispense quantities and time delays that allow for pipet changing and pipet manipulation. The pipetter then performs these customized programming steps for up to a predetermined number of cycles. This even more complicated mode is presented to the operator as the fifth operating mode, after the sequential-dispensing mode. As should now be evident, the operating modes are presented in the order of complexity, from simplest to most difficult. In this way, the operator knows intuitively, without requiring any guidance from an operating manual, how complex any operating mode is.

To enter the hands-free mode, the operator presses the mode key until the hands-free mode symbol appears on the LCD. The operator then presses the enter key to enter the hands-free mode into the computer. Next, the LCD asks the operator to program the desired pipet size. To locate the desired pipet size, the operator presses the down or up scroll keys. After the operator has selected the pipet size, the operator presses the enter key to enter that information into the computer. Next, the LCD asks the operator to program the dispensing aliquot volume. To locate the desired dispensing aliquot volume, the operator presses the down or up scroll keys. After the operator has selected the dispensing aliquot volume, the operator presses the enter key to enter that information into the computer. Next, the LCD asks how many times, i.e, cycles, the operator will need to aspirate and dispense. The operator selects the number of desired cycles by pressing the up scroll key. After reaching the desired number of cycles, the operator presses the enter key to enter that information into the computer.

In this mode, the operator must select and enter a number of delays. The LCD first displays a "delA" symbol, which is a request by the computer to enter the time delay between cycles, that is, the time between blowout and the next aspiration. The cycle time delay should be long enough to allow the operator to change the pipet or tip for the next aspiration. The operator presses the up scroll key until the desired time delay is located, and then presses the enter key to enter that information into the computer. For example, the available time delay between cycles may range from 1 second to 99 seconds. Usually 10 seconds is plenty of time to change the pipet. As the operator becomes more experienced changing pipets, the time delay can be reduced. After the cycle delay is entered, the LCD displays a "delY" symbol requesting that the aliquot time delay between dispensing aliquots be selected and entered. This delay is programmed in similar fashion as the cycle delay. Usually a 1 or 2 second delay is plenty of time to move from one tissue culture dish, vessel or well to another. The LCD then displays a "bdly" symbol indicating that the blowout time delay between each pipet's last dispensing aliquot and blowout is to be selected and entered. This delay is programmed in similar fashion as the cycle and aliquot delays. Usually a 1 to 3 second delay is required to move from the tissue culture dish over to the waste reservoir in which the blowout is emptied.

After all the pipet, aliquot, cycle and time delay information has been entered into the computer, the computer causes the LCD to display the "begin" symbol, which tells the operator that the first aspiration may begin. The operator then submerges the pipette into the liquid medium and aspirates the liquid medium by pressing either operating button. No other button thereafter requires pressing (hence the label "hands-free" mode), unless the operator wishes to pause or stop the operation. The computer now generates control signals to cause the aspirating mechanism to fill the pipet with the precise fluid volume automatically.

After the pipet is automatically filled, the computer will automatically display the remaining cycle count. The operator then removes the pipet from the media bottle. The computer generates a control signal to the dispensing mechanism to dispense automatically the desired aliquots, at the programmed aliquot time delay between each aliquot, the operator moving the pipet or tip, for example, from well to well. After the last aliquot of the first cycle is dispensed, the operator moves the pipet or tip to the waste reservoir. The computer causes the dispensing mechanism, after the programmed blowout delay, to blowout the fluid remaining in the pipet into the waste reservoir automatically. The operator then, if desired, changes the pipet, and resubmerges the pipet into the liquid medium. After the cycle time delay has expired, the computer causes the aspirating mechanism to again fill the pipet with the precise fluid volume automatically. The remaining cycle count decrements by one and is displayed, and the next cycle is performed automatically by the pipetter, and this continues until the last blowout of the final cycle has occurred. At that point, the LCD displays the "begin" symbol to indicate that the pipetter is ready for the next group of cycles.

As before, any programming errors or changes in operating parameters may be done by the operator pressing the "oops" key, as described above. The operator may pause the hands-free mode operation by pressing either operating button, and then restart the operation in the same manner. The operator may stop the hands-free operation by pressing both operating buttons simultaneously. The LCD will show a "stop" symbol, and the operator presses either operating button to show the "blowout" symbol. If either operating button is pressed again, the computer will cause the dispensing mechanism to blowout any remaining liquid.

A memory, such as RAM, is connected to the microprocessor computer in a conventional fashion so that the operator can save the programmed parameters, especially in the multi-dispense, sequential dispense and hands-free modes. To store the programming parameters, the operator presses the mode key until the desired operating mode is reached. However, the operator does not yet press the enter key to enter the operating mode. Instead, the operator presses the up scroll key to enable the memory function. Of course, it is understood that another programming key may be provided to directly enter the memory programming mode. Next, the operator selects a desired program number for the parameters to be entered. For example, the operator may select programming number 001, 002 or 003 by using the up scroll button. The operator presses the enter key to enter the selected programming number. The computer will cause the LCD to request the desired pipet size. The operator uses the up scroll key to select the desired pipet size and presses the enter key to enter this parameter into the memory. The computer will next cause the LCD to request the desired aliquot volume. The operator uses the up scroll key to select the desired aliquot volume and presses the enter key to enter this parameter into the memory. All other parameters, such as number of cycles, etc., may be selected and entered into memory in this fashion. When all the parameters have been entered, the operator presses the enter key to complete the memory programming.

To access the stored parameters, the operator presses the mode key, but does not press the enter key. The operator then presses the up scroll key to the desired program number, for example, 001, 002, or 003, and presses enter. The pipetter is activated by pressing either operating button, and will operate in accordance with the stored parameters. To change the programs stored in memory, the desired program is accessed as described above, but the program is not activated. The operator uses the "oops" key as described above to access the old parameter data, and selects and enters the new parameter data. When all the data has been changed, the operator then presses the enter key to store the changed program into memory.

Of course, it will be appreciated that the invention may take forms other than those specifically described, and the scope of the invention is to be determined solely by the following claims.

What is claimed is:

1. A method for placing a computer controlled electronic pipetter in a manual mode of operation so as to simulate manually controlling said electronic pipetter, said electronic pipetter having a first button for aspirating fluid and a second button for dispensing fluid through a pipette attached to said electronic pipetter and a computer control for controlling said manual mode of said electronic pipetter, wherein said method comprises the steps of:

turning the electronic pipetter on;

activating said computer control into said manual mode of operation;

submerging the pipette into the fluid;

pressing the first button to cause the electronic pipetter to aspirate the fluid;

removing the pipette from the fluid; and pressing the second button to cause the electronic pipetter to dispense the aspirated fluid wherein the speeds of aspirating and dispensing are respectively sensitive to the pressures applied to the first and second buttons and wherein said computer control places said electronic pipetter in a manual mode of operation to provide for controlling said speeds of aspirating and dispensing so as to simulate manual control of said electronic pipetter.

* * * * *